United States Patent [19]
Helmut et al.

[11] Patent Number: 5,260,247
[45] Date of Patent: Nov. 9, 1993

[54] CATALYTIC COMPOSITION FOR OXYCHLORINATION AND PROCESS FOR THE OXYCHLORINATION OF ETHYLENE USING SUCH A COMPOSITION

[75] Inventors: Derleth Helmut, Nienburg, Fed. Rep. of Germany; Strebelle Michel, Brussels, Belgium

[73] Assignee: Solvay (Société Anonyme), Brussels, Belgium

[21] Appl. No.: 814,453

[22] Filed: Dec. 30, 1991

[30] Foreign Application Priority Data

Jan. 11, 1991 [BE] Belgium .................. 09100025
Jul. 10, 1991 [BE] Belgium .................. 09100659

[51] Int. Cl.$^5$ .................. B01J 27/122; B01J 27/138
[52] U.S. Cl. .................. 502/225; 502/226; 570/224
[58] Field of Search .................. 502/225, 226

[56] References Cited

U.S. PATENT DOCUMENTS

| | | | |
|---|---|---|---|
| 3,624,170 | 11/1971 | Wakiyama et al. | 502/225 X |
| 4,124,534 | 11/1978 | Leitert et al. | 502/225 |
| 4,194,990 | 3/1980 | Pieters et al. | 502/225 |
| 4,278,563 | 7/1981 | Fremont et al. | 502/225 |
| 4,414,136 | 11/1983 | Convers | 502/225 |
| 4,424,143 | 1/1984 | Shiozaki et al. | 502/225 |
| 4,910,354 | 3/1990 | Derleth et al. | 570/243 |
| 5,004,849 | 4/1991 | Hirschmann et al. | 502/225 X |
| 5,011,808 | 4/1991 | Scott | 502/225 |
| 5,070,062 | 12/1991 | Canavesi et al. | 502/225 |
| 5,132,259 | 7/1992 | Curnutt | 502/225 X |

FOREIGN PATENT DOCUMENTS 0206265 12/1986 European Pat. Off.
0278922 8/1988 European Pat. Off.

*Primary Examiner*—Patrick P. Garvin
*Attorney, Agent, or Firm*—Spencer, Frank & Schneider

[57] ABSTRACT

The invention relates to a catalytic composition for oxychlorination, as well as to a process for the oxychlorination of ethylene by means of such a catalytic composition based on copper chloride, magnesium chloride, lithium chloride and at least one other alkali metal chloride, deposited on an inert support. The oxychlorination thus carried out enables an excellent yield to be obtained without the catalytic composition sticking to the walls of the reactor and without the latter being corroded by the catalytic composition employed.

9 Claims, No Drawings

CATALYTIC COMPOSITION FOR OXYCHLORINATION AND PROCESS FOR THE OXYCHLORINATION OF ETHYLENE USING SUCH A COMPOSITION

The present invention relates to a catalytic composition for oxychlorination and to a process for the oxychlorination of ethylene using such a catalytic composition.

Oxychlorination, that is to say the chlorination of hydrocarbons with hydrogen chloride in the presence of air or oxygen, constitutes a reaction which has been known for a long time and which is usually performed in the presence of catalysts consisting of metal salts deposited on inert supports such as aluminas, silica gels, mixed oxides or alternatively clays or other supports of natural origin. Industrially, the catalyst is used most frequently in a fluidised bed, but may also be employed in a fixed bed. As metal salts, halides such as copper chloride are most often used. When it is used alone, copper chloride possesses, however, the drawback of being relatively volatile, which leads to a fall in catalytic activity and in the yield of the oxychlorination reaction which is unacceptable in industrial installations.

It is well known to improve the performance of oxychlorination catalysts consisting of copper chloride on a support by adding alkali metal, alkaline earth metal or rare earth metal (lanthanide) chlorides. The addition of alkali metal chlorides is said to increase the selectivity of the reaction, in particular by limiting the side reactions of oxidation of ethylene to $CO$ and $CO_2$. Magnesium chloride is used, in particular, for the purpose of improving the fluidisation of the catalyst.

Catalytic compositions for oxychlorination simultaneously comprising copper chloride, magnesium chloride and alkali metal chlorides on an inert support have already been proposed.

U.S. Pat. No. 3,624,170 (TOYO SODA) describes a ternary catalytic composition based on copper chloride, sodium chloride and magnesium chloride (in specific amounts), which composition is said to avoid, in addition, the deactivation caused by contamination with $Fe_2Cl_6$ which would be present when stainless steel reactors are used.

Patent application EP-A-0375202 (ICI) describes a ternary catalytic composition based on copper chloride, magnesium chloride and potassium chloride, employed in proportions such that the Cu/Mg/K atomic ratio is preferably 1:0.2–0.9:0.2–0.9.

Patent application EP-A-0255156 (SOLVAY) describes ternary catalytic compositions containing a mixture of copper chloride, magnesium chloride and an alkali metal chloride chosen from sodium chloride or lithium chloride, used in precise proportions which enable a very good yield to be achieved in a fluidised bed process for the oxychlorination of ethylene to 1,2-dichloroethane, simultaneously reducing the corrosion of stainless steel reactors as a result, in particular, of a reduction in the sticking and clumping of the particles of catalyst. This document teaches that, for ternary compositions containing copper chloride, magnesium chloride and sodium chloride as an alkali metal chloride, an Na/Cu atomic ratio above 0.2:1 leads to problems of corrosion of the reactor. In contrast, if lithium is used as an alkali metal, no corrosion phenomenon is seen over a wide range of Li/Cu atomic ratios. However, the examples show the appearance of problems of sticking and clumping of the catalyst with compositions containing lithium in an Li/Cu ratio above 0.6.

It has recently been observed that even the apparently fluidisable and stable compositions of the prior art possess, after a few months of industrial use, a tendency to stick to the wall of the reactor, thereby constituting a considerable impediment to their use, whereas these terndry catalytic compositions afford, moreover, excellent performance from the standpoint of activity and selectivity of the oxychlorination reaction. Any decrease in the amount of alkali metal chloride in the ternary catalytic composition for the purpose of avoiding these problems of sticking inopportunely causes a fall in selectivity and hence in the yield of 1,2-dichloroethane.

An especially efficacious catalytic composition which enables a high yield to be achieved, phenomena of sticking or clumping of the catalyst or of corrosion of the reactor no longer being encountered, has now been found. This catalytic composition is especially suitable for fluidised bed oxychlorination processes.

The present invention relates to a catalytic composition for oxychlorination comprising copper chloride, magnesium chloride and lithium chloride deposited on an inert support, characterized in that it contains, in addition, at least one alkali metal chloride other than lithium chloride. It also relates to a process for the oxychlorination of ethylene to 1,2-dichloroethane, characterized in that the oxychlorination reaction is catalysed by the catalytic composition according to the invention.

Surprisingly, it has been observed that catalytic compositions containing, in addition to copper chloride, magnesium chloride and lithium chloride, at least one alkali metal chloride other than lithium chloride enable a yield to be achieved which has never yet been obtained without encountering the drawbacks described above with ternary compositions of the prior art.

As examples of other alkali metal chlorides which are usable, sodium, potassium, rubidium and cesium chlorides may be mentioned. Sodium chloride, potassium chloride and mixtures of sodium chloride and potassium chloride are nevertheless preferably used.

The catalytic compositions according to the invention generally possess a copper content, calculated in the form of the metal relative to the total weight of the catalytic composition, of at least 30 g/kg and most often at least 40 g/kg. It does not in general exceed 90 g/kg and most often does not exceed 70 g/kg. Preferably, the amount of copper chloride is at least 50 g/kg. Preferably, it does not exceed 65 g/kg.

The content of the other salts in the catalytic compositions may be readily deduced from the copper contents thus specified, in combination with the atomic ratios specified below.

The proportions (expressed as the atomic ratio of the metals) in which copper chloride, magnesium chloride, lithium chloride and the other alkali metal chloride(s) are employed are defined as follows:

The Mg/Cu atomic ratio is generally at least 0.1. It is preferably at least 0.3. This ratio does not in general exceed 1.5. In preferred compositions, this Mg/Cu ratio does not exceed 1.0.

The Li/Cu atomic ratio is generally at least 0.01. It is preferably at least 0.1. Under the most especially preferred conditions, it is at least 0.15. This ratio does not in general exceed 1.0. In preferred compositions, this Li/Cu ratio does not exceed 0.8. Under the most especially preferred conditions, it does not exceed 0.6.

The atomic ratio of each of the alkali metals other than lithium to copper is generally at least 0.001. It is preferably at least 0.01. Under the most especially preferred conditions, it is at least 0.03. This ratio does not in general exceed 0.8. In preferred compositions it does not exceed 0.6. Under the most especially preferred conditions it does not exceed 0.4.

The catalytic composition according to the invention are hence characterized by Cu/Mg/Li/other alkali metal(s) atomic ratios of 1:0.1–1.5:0.01–1.0:0.001–0.8. According to a preferred embodiment of the present invention, the atomic ratio of the sum of all the alkali metals (including lithium) to copper does not exceed 1.5. Under especially preferred conditions, this ratio does not exceed 1.2. Under the most especially preferred conditions, it does not exceed 0.8.

Preferably, the atomic ratio of each of the alkali metals other than lithium to lithium is between 0.1 and 2.0. As a special preference, this ratio is between 0.2 and 1.5.

The support used for the catalytic compositions according to the invention is chosen from inert supports such as aluminas, silica gels, mixed oxides or alternatively clays or other supports of natural origin. Preferably, the support for the catalytic compositions of the invention is an alumina. The alumina employed in the catalytic compositions of the invention can be of any origin and be obtained according to any known process; aluminas of the $\eta$ or $\gamma$ type are customarily used. Good results have been obtained with a $\gamma$ alumina.

The alumina generally employed in the catalytic compositions of the invention possesses an average particle diameter of between 10 and 200 $\mu$m, and preferably an average diameter of between 20 and 120 $\mu$m.

The specific surface area of the alumina, measured according to the BET method, is generally between 50 $m^2/g$ and 250 $M^2/g$. Good results have been obtained with an alumina having a specific surface area of between 100 $m^2/g$ and 210 $M^2/g$.

Finally, the pore volume of the aluminas customarily used lies between 0.1 and 1 $cm^3/g$. Preferably, the pore volume is between 0.2 and 0.8 $cm^3/g$, and good results have been obtained with an alumina having a pore volume lying between 0.3 and 0.6 $CM^3/g$.

It should be noted that alumina, by virtue of its nature and its method of synthesis, contains a greater or lesser amount of alkali metal atoms, in particular of sodium, capable of being integrated in the crystal network or of being bound in some or other chemical form. Depending on the nature of the alumina, the latter can conventionally contain from 20 to 5000 ppm of alkali metals. The presence of these alkali metal atoms which can be more readily qualified as "non-washable", is not taken into account for determination of the alkali metal content in the catalytic compositions according to the present invention, which relates exclusively to the alkali metals added in the form of salts to form the catalytic composition and which can be considered as constituting "washable alkali metals". These alkali metal salts are not chemically bound to the alumina support and are generally introduced into the catalytic compositions by impregnation of the alumina with the salts in question. This impregnation with the desired alkali metals salts may be carried out either at the same time as the impregnation with the other salts, or before or after this impregnation.

The method of obtaining the catalytic compositions according to the invention is not critical.

The metal chlorides may be introduced into the catalytic composition either directly in the form of chlorides, for example by impregnation of the support using a solution containing a mixture of these salts, or in the form of other compounds of the metals, such as oxides, hydroxides, nitrates or any other compound capable of being converted to a chloride under the conditions in which oxychlorination reactions are performed.

A method of obtaining the compositions which has given good results consists in impregnating an alumina with an aqueous solution containing the appropriate amounts of copper chloride, magnesium chloride, lithium chloride and the chlorides of the other desired alkali metals. The appearance of a liquid phase not adsorbed by the solid is avoided by limiting the volume of the impregnated solution to 70 to 100% of the pore volume of the amount of alumina employed. This impregnated alumina is then dried before being introduced into the actual oxychlorination reactor.

Another method of preparation which is usable for preparing catalytic compositions according to the invention consists in mixing two different catalytic compositions, for example a ternary composition containing copper chloride, magnesium chloride and lithium chloride with a binary catalytic composition based on copper chloride and potassium chloride, in proportions such that a catalytic composition according to the invention containing, overall, copper chloride, magnesium chloride, lithium chloride and potassium chloride with the requisite amounts of the different metal chlorides and the desired atomic ratios is obtained. Other mixtures of different catalytic compositions can be produced.

The final catalytic compositions generally possess a BET specific surface area of between 25 $m^2/g$ and 200 $m^2/g$, and preferably between 50 and 150 $m^2/g$. Good results have been obtained with catalytic compositions having a BET specific surface area of between 80 and 140 $m^2/g$.

The catalytic compositions are especially advantageous in an oxychlorination process in which the catalyst is in the form of a fluidised bed, on account of an improved yield. They can also be employed in an oxychlorination process carried out with a catalyst arranged in a fixed bed, subject to the particles of catalyst being prepared in a suitable form, for example in the form of granules a few mm in diameter.

The molecular oxygen needed for the oxychlorination reaction is introduced into the reactor either dilute, for example in the form of air, or pure. Pure oxygen is understood to mean essentially undiluted. The use of pure oxygen is especially advantageous, since it enables the unconverted reactants to be recycled into the reactor and limits the amount of gases to be treated at the outflow from the reactor.

The catalytic compositions according to the invention are most especially suitable for a process for the oxychlorination of ethylene to 1,2-dichloroethane in which the catalyst is in the form of a fluidised bed and in which the oxygen is introduced in pure form.

When the process is carried out with a catalyst arranged in a fluidised bed, the temperature at which the oxychlorination reaction is performed usually lies between 200° and 300° C. Preferably, this temperature is between 220° and 280° C. Finally, good results have been obtained with a temperature lying in the region of 240° C.–270° C.

The pressure at which the oxychlorination reaction is performed is not in itself critical. Usually, it is carried out at pressures of between 0.1 and 1 MPa, and preferably at pressures of between 0.1 and 0.8 MPa.

The rate of fluidisation of the catalytic compositions is not in itself critical, and depends essentially on the particle size of the catalyst and the dimensions of the apparatus. Generally, the process is carried out using rates of between 5 and 100 cm/s.

Finally, the ratio of the reactants employed is the same as that generally used in the earlier processes. It is customary to work with a slight excess of ethylene relative to the amount of HCl employed. However, the catalytic compositions of the invention also make it possible to work in the vicinity of stoichiometry, or even with an excess of HCl.

The invention is more fully illustrated by the examples which follow:

The examples designated (c) relate to examples given by way of comparison.

EXAMPLES 1 to 8

A sample of a catalytic composition corresponding to example 1(C) is prepared with a gamma alumina the characteristics of which are as follows: specific surface area = 186 m$^2$/g; pore volume = 0.38 cm$^3$/g; free-flow density 0.75 kg/dm$^3$; average particle diameter = 50 μm. An aqueous impregnation solution comprising, in the dissolved state, 162 g of CuCl$_2$.2H$_2$, 143 g of MgCl$_2$.6H$_2$O and 21 g of LiCl is added to approximately 800 g of this alumina. The wet solid is then heated to 150° C. 1 kg of catalyst is thereby obtained with, calculated in the form of the metal relative to the total weight of the catalyst, a copper content of 60 g/kg, a magnesium content of 17 g/kg and a lithium content of 3.3 g/kg. Expressed in terms of atomic ratio, the proportion of the different metals Cu/Mg/Li is 1:0.74:0.50.

Examples 2(c), 3(c) and 4(c) are prepared in the same manner, starting with the same alumina impregnated with aqueous solutions containing the three desired metal chlorides, CuCl$_2$.2H$_2$O, MgCl$_2$.6H$_2$O and NaCl or KCl, in appropriate amounts and proportions.

Examples 5 to 7, according to the invention, are prepared in the same manner, starting with the same alumina impregnated with an aqueous solution containing CuCl$_2$.2H$_2$O, MgCl$_2$.6H$_2$O, LiCl and KCl or NaCl in appropriate amounts and proportions.

Example 8 is prepared by mechanically mixing two ternary compositions, one containing copper chloride, magnesium chloride and lithium chloride, and the other copper chloride, magnesium chloride and sodium chloride.

The contents of these different catalytic compositions are recorded in Table 1 below.

TABLE 1

| Example Number | Metal content (g/kg) | | | | | Atomic proportions of the metals | | | | |
|---|---|---|---|---|---|---|---|---|---|---|
| | Cu | Mg | Li | Na | K | Cu | Mg | Li | Na | K |
| 1(c) | 60 | 17 | 3.3 | — | — | 1 | 0.74 | 0.50 | — | — |
| 2(c) | 60 | 17 | — | 6.2 | — | 1 | 0.74 | — | 0.29 | — |
| 3(c) | 58 | 17 | — | — | 11 | 1 | 0.77 | — | — | 0.31 |
| 4(c) | 59 | 17 | — | — | 17 | 1 | 0.75 | — | — | 0.47 |
| 5 | 57 | 16 | 1.6 | — | 12 | 1 | 0.73 | 0.26 | — | 0.34 |
| 6 | 60 | 17 | 2.0 | 2.7 | — | 1 | 0.74 | 0.31 | 0.12 | — |
| 7 | 56 | 16 | 3.0 | 2.0 | — | 1 | 0.75 | 0.49 | 0.10 | — |

TABLE 1-continued

| Example Number | Metal content (g/kg) | | | | | Atomic proportions of the metals | | | | |
|---|---|---|---|---|---|---|---|---|---|---|
| | Cu | Mg | Li | Na | K | Cu | Mg | Li | Na | K |
| 8 | 48 | 13.5 | 1.3 | 0.8 | — | 1 | 0.74 | 0.25 | 0.05 | — |

EXAMPLES 9 to 16

225 cm$^3$ Of the catalytic compositions described in Examples 1 to 8 are arranged in an Inconel 600 reactor for the fluidised bed oxychlorination of ethylene to 1,2-dichloroethane (DCEa).

The reactant gases are introduced into this reactor at the bottom through a sintered metal filter. The working conditions under which these examples are carried out are as follows:

flow rate of the reactants (lN/h) C$_2$H$_4$/HCl/Air: 84/160/260
temperature: 255° C.
pressure: 0.6 MPa
fluidisation rate: 10 cm/s
contact time: 5 s The yields obtained in these laboratory tests are limited by the restricted residence time of 5 s. The conversion of C$_2$H$_4$ is accordingly limited in all the tests (the operating conditions of an industrial reactor enable markedly longer residence times, namely 10 to 80 s and most often from 20 to 50 s, to be achieved, in order to effect a better conversion of ethylene). The selectivity results obtained are, however, entirely significant for comparing the performances of the different catalytic compositions.

The reaction products are then expanded to atmospheric pressure via a reactor pressure regulation valve. The reaction products are then cooled in a trap maintained at −20° C. and the uncondensed gases are washed in a water scrubber before sweeping into a sampling bulb. The evaluation of the products formed is carried out on the basis of chromatographic analyses of the liquid and gaseous products collected and titration of the acidity of the aqueous solution collected at the foot of the scrubber.

The tendency of the catalytic compositions to stick is measured in a micro-pilot-scale reactor operating under the same working conditions as the reactor described above, but equipped with an internal tube (glove finger) through which an oil passes, the latter being maintained at a temperature lower than the temperature at which the reaction is carried out. The tendency to stick is determined visually by examination of this internal tube after 20 hours of operation.

The results of Examples 9 to 16, corresponding to the 8 tests carried out with the catalytic compositions 1 to 8, are collated in Table 2.

TABLE 2

| Example Number | Origin of the catalytic compositions | DCEa yield relative to HCl (mol %) | Selectivity with respect to ethylene converted (mol %) | | | Tendency to stick |
|---|---|---|---|---|---|---|
| | | | DCEa | EtCl | CO + CO$_2$ | |
| 9(c) | Ex. 1(c) | 96.6 | 98.0 | 0.3 | 1.0 | YES |
| 10(c) | Ex. 2(c) | 98 | 96.3 | 0.6 | 2.0 | YES |
| 11(c) | Ex. 3(c) | 98.6 | 97.5 | 0.25 | 1.5 | YES |
| 12(c) | Ex. 4(c) | 97.8 | 98.0 | 0.2 | 0.8 | YES |
| 13 | Ex. 5 | 98.3 | 97.8 | 0.1 | 1.2 | NO |
| 14 | Ex. 6 | 98.5 | 97.7 | 0.1 | 1.5 | NO |
| 15 | Ex. 7 | 98.5 | 97.2 | 0.1 | 2.0 | NO |

TABLE 2-continued

| Example Number | Origin of the catalytic compositions | DCEa yield relative to HCl (mol %) | Selectivity with respect to ethylene converted (mol %) | | | Tendency to stick |
| --- | --- | --- | --- | --- | --- | --- |
| | | | DCEa | EtCl | CO + CO$_2$ | |
| 16 | Ex. 8 | 97.1 | 98.0 | 0.2 | 1.0 | NO |

The catalytic compositions of comparative Examples 1 to 4, the results of which with respect to oxychlorination and sticking are recorded in Examples 9 to 12, give very good selectivity for conversion of ethylene to 1,2-dichloroethane, but cause sticking to the walls of the reactor. In contrast, Examples 13 to 16 demonstrate that the compositions according to the invention enable a good yield of 1,2-dichloroethane with respect to HCl and very good selectivity for 1,2dichloroethane to be obtained without phenomena of sticking being manifested.

We claim:

1. Catalytic composition for oxychlorination comprising copper chloride, magnesium chloride and lithium chloride deposited on an inert support, characterized in that it contains, in addition, at least one alkali metal chloride other than lithium chloride.

2. Catalytic composition according to claim 1, characterized in that the alkali metal chloride is chosen from sodium chloride, from potassium chloride and mixtures thereof.

3. Catalytic composition according to claim 1, characterized in that the alkali metal chloride is sodium chloride.

4. Catalytic composition according to claim 1, characterized in that the alkali metal chloride is potassium chloride.

5. Catalytic composition according to claim 1, characterized in that the alkali metal chloride is a mixture of sodium chloride and potassium chloride.

6. Catalytic composition according to any claim 1, characterized in that its copper content is between 30 and 90 g/kg.

7. Catalytic composition according to claim 1, characterized by Cu/Mg/Li/other alkali metal(s) atomic ratios of 1:0.1–1.5:0.01–1.0:0.001–0.8.

8. Catalytic composition according to claim 1, characterized in that the atomic ratio of the sum of all the alkali metals to copper does not exceed 1.5.

9. Catalytic composition according to claim 1, characterized in that the support is an alumina.

* * * * *